(12) United States Patent
McFarland et al.

(10) Patent No.: US 8,617,859 B2
(45) Date of Patent: Dec. 31, 2013

(54) C4 DICARBOXYLIC ACID PRODUCTION IN FILAMENTOUS FUNGI

(75) Inventors: Sarah McFarland, Sacramento, CA (US); Amanda Fischer, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/702,026

(22) PCT Filed: Jun. 2, 2011

(86) PCT No.: PCT/US2011/038881
§ 371 (c)(1),
(2), (4) Date: Dec. 18, 2012

(87) PCT Pub. No.: WO2011/153317
PCT Pub. Date: Dec. 8, 2011

(65) Prior Publication Data
US 2013/0089902 A1    Apr. 11, 2013

Related U.S. Application Data

(60) Provisional application No. 61/351,425, filed on Jun. 4, 2010.

(51) Int. Cl.
*C12N 9/00* (2006.01)

(52) U.S. Cl.
USPC ........................................ 435/145; 435/254.3

(58) Field of Classification Search
USPC ............................................. 435/145, 254.3
See application file for complete search history.

(56) References Cited

U.S. PATENT DOCUMENTS

| 3,063,910 A | 11/1962 | Abe et al. |
| 5,536,661 A | 7/1996 | Boel et al. |
| 7,504,490 B1 | 3/2009 | Weinstock et al. |

FOREIGN PATENT DOCUMENTS

| EP | 2471943 A1 | 7/2010 |
| WO | 2007061590 A1 | 5/2007 |
| WO | 2008144626 A1 | 11/2008 |
| WO | 2009011974 A1 | 1/2009 |
| WO | 2009065778 A1 | 5/2009 |
| WO | 2009155382 A1 | 12/2009 |
| WO | 2010003728 A1 | 1/2010 |
| WO | 2010111344 A2 | 9/2010 |
| WO | 2011024583 A1 | 3/2011 |
| WO | 2011028643 A1 | 3/2011 |
| WO | 2011066304 A2 | 6/2011 |

OTHER PUBLICATIONS

Ludwig et al, 1998, Plant Physiol 117 (3), 1071-1081.
WO 2011-024583—Eng Equiv—EP 2 471 943.
Fedorova et al, 2007, UniProt Access No. A1C406.
Battat 1991, Biotechnol Bioeng 37, 1108-1116.
Bauer 1999, FEMS Microbiol Lett 179, 107-113.
Bercovitz 1990, Appl Environ Microbiol 56, 1594-1597.
Camarasa 2001, Appl Environ Microbiol 67(9), 4144-4151.
Fedorova 2008, PLoS Genetics 4(4), 1-13.
Grobler 1995, Yeast 11, 1485-1491.
Nierman 2005, Nature 438 (22), 1151-1156.
Peleg 1988, Appl Microbiol Biotechnol 28, 69-75.
Pines 1997, Appl Microbiol Biotechnol 48, 248-255.
Sauer 2008, Trends Biotechnol 26, 100-108.
Zelle 2008, Appl Environ Microbiol 74, 2766-2777.
Machida et al 2006, Uniprot Access No. Q2UGL1.
Machida et al 2006, Uniprot Access No. Q2USG3.
Birren et al, 2008, UniProt Access No. B6JXU3.
Elleuche et al, 2009, Curr Genet 55, 211-222.
Goldberg et al, 2006, J Chem Technol Biotechnol 81(10), 1601-1611.
Nevoigt, 2008, Microbiol Mol Biol Revs 72(3), 379-412.
Nielsen et al, 2008, FEMS Yeast Res 8, 122-131.
Bush et al., 2010, GENESEQ, Access No. AWP70496.
Winkler et al., 2009, GENESEQ, Access No. ATT44026.
Nierman et al, 2005, UniProt Access No. Q4WCF3.
Lubertozzi et al, 2008, Biotechnol Advances 27, 53-75.
Nierman et al, 2008—Genbank, Access No. XM_001276571.
Whisstock et al 2003 Qtr Rev Biophys 36(3) 307-340.
Zelle, 2011, PhD Thesis, Delft University of Technology, Delft.

*Primary Examiner* — Tekchand Saidha
*Assistant Examiner* — Rama P Ramanujam
(74) *Attorney, Agent, or Firm* — Eric J. Fechter

(57) ABSTRACT

The present invention relates to methods of producing C4 dicarboxylic acids, such as malic acid, comprising: (a) cultivating a host cell comprising a polynucleotide encoding a C4 dicarboxylic acid transporter; and (b) recovering the C4 dicarboxylic acid. The present invention also relates to methods for increasing C4 dicarboxylic acid production, as well as host cells comprising the polynucleotides.

28 Claims, 5 Drawing Sheets

```
         M   S   S   E   T   P   T   Y   S   S   W   A   S   Q   R   Y   N   E   L   I
CO     1 ATGTCGTCGG AGACACCGAC ATACTCCTCC TGGGCATCCC AGAGGTACAA CGAATTGATT
WT     1 ATGTCTTCGG AAACGCCGAC TTACAGCTCT TGGGCGAGCC AACGGTACAA CGAATTGATC
         A   W   N   V   K   G   P   R   L   P   I   A   Q   R   L   K   H   F   T   W
CO    61 GCATGGAACG TCAAGGGTCC GAGGTTGCCC ATCGCACAGA GGCTCAAGCA CTTCACGTGG
WT    61 GCTTGGAACG TCAAGGGTCC TCGCTTACCC ATTGCCCAGC GTCTAAAACA CTTCACTTGG
         S   W   F   T   C   T   M   A   T   G   G   V   G   M   I   L   A   S   L   P
CO   121 TCGTGGTTCA CGTGTACTAT GGCAACAGGC GGTGTCGGAA TGATCCTCGC GTCGCTCCCC
WT   121 TCCTGGTTTA CCTGTACCAT GGCCACCGGT GGTGTCGGTA TGATTCTGGC ATCGCTGCCC
         Y   R   F   T   G   L   N   T   I   G   K   V   V   F   I   F   Q   V   V   L
CO   181 TATAGGTTCA CGGGCTTGAA CACCATCGGA AAGGTCGTCT TCATTTTCCA GGTGGTCTTG
WT   181 TACCGATTCA CAGGCTTAAA CACGATTGGT AAAGTCGTGT TCATTTTCCA GGTCGTTTTG
         L   A   I   F   C   S   A   M   A   F   R   F   I   R   Y   P   E   T   F   K
CO   241 TTGGCCATCT TCTGTTCGGC CATGGCCTTC AGGTTCATTC GCTACCCGGA GACTTTCAAG
WT   241 CTGGCGATTT TCTGTTCGGC GATGGCCTTT CGGTTCATTC GTTACCCCGA AACCTTCAAA
         K   S   I   Y   H   H   L   E   K   L   F   I   G   T   F   L   L   S   M   S
CO   301 AAGTCGATCT ATCACCACTT GGAGAAATTG TTCATCGGTA CATTCTTGCT CTCGATGTCG
WT   301 AAGTCTATTT ACCATCATTT GGAGAAGCTC TTCATTGGTA CCTTCCTGCT TTCCATGTCG
         T   F   I   D   M   L   A   A   Y   G   Y   P   S   T   G   E   W   M   V   Y
CO   361 ACCTTCATCG ATATGCTCGC AGCCTACGGC TATCCTTCCA CCGGTGAATG GATGGTGTAC
WT   361 ACGTTCATCG ATATGCTCGC CGCCTACGGA TACCCCAGCA CTGGCGAGTG GATGGTGTAC
         L   I   R   I   F   Y   W   M   Y   A   A   V   S   F   V   Y   A   I   F   A
CO   421 TTGATCCGAA TCTTCTACTG GATGTACTTC GCCGTCTCCT TCGTCTACGC GATCTTCGCA
WT   421 CTAATTCGCA TTTTTTACTG GATGTACTTT GCCGTCTCGT TCGTATACGC CATCTTCGCA
         F   A   T   T   F   H   M   H   P   Y   T   L   E   T   A   S   P   A   W   I
CO   481 TTCGCAACTA CTTTCCATAT GCATCCTTAT ACCCTCGAAA CGGCATCGCC TGCCTGGATC
WT   481 TTTGCTACCA CCTTTCACAT GCATCCCCTAC ACCCTGGAGA CGGCTCCTGC AGCATGGATT
         L   P   I   F   P   A   M   I   S   G   A   V   A   G   T   V   A   F   T   Q
CO   541 CTCCCGATTT TCCCTGCGAT GATCTCCGGA GCAGTGGCAG GAACCGTGGC ATTCACTCAG
WT   541 CTGCCTATTT TCCCAGCTAT GATTAGCGGC GCTGTCGCCG GTACTGTGGC CTTCACACAA
         P   P   H   Q   L   K   N   L   V   V   C   G   I   M   F   Q   G   L   G   F
CO   601 CCTCCCCATC AGCTCAAAAA CCTCGTGGTG TGTGGCATTA TGTTCCAGGG TTTGGGCTTC
WT   601 CCGCCGCACC AATTGAAGAA TTTGGTCGTG TGCGGTATCA TGTTCCAGGG CTTGGGTTTC
         W   V   Y   I   M   L   F   A   V   N   M   L   K   L   F   T   K   G   M   M
CO   661 TGGGTCTACA TCATGTTGTT CGCGGTCAAC ATGCTCAAAT TGTTCACAAA GGGCATGATG
WT   661 TGGGTGTACA TCATGCTGTT CGCCGTGAAC ATGCTCAAGC TGTTTACGAA GGGTATGATG
         G   A   S   E   R   P   G   L   F   M   F   V   G   P   P   A   Y   T   G   L
CO   721 GGAGCCTCGG AACGACCGGG TTTGTTCATG TTCGTCGGAC CTCCGGCATA CACAGGCCTC
WT   721 GGTGCCTCTG AACGCCCTGG TCTTTTTATG TTCGTTGGTC CTCCGGCCTA TACCGGCTTG
         A   L   I   G   M   G   K   T   A   M   D   S   K   I   S   M   F   S   A   T
CO   781 GCCCTCATCG GTATGGGCAA GACCGCCATG GATTCCAAAA TCTCCATGTT CTCCGCCACT
WT   781 GCTTTAATCG GTATGGGTAA AACTGCTATG GACTCCAAGA TCTCCATGTT TTCTGCAACC
         P   V   S   S   E   H   L   A   F   M   C   T   F   M   A   L   F   M   W   G
CO   841 CCCGTCTCCT CCGAACACCT CGCATTCATG TGTACCTTCA TGGCACTCTT CATGTGGGGT
WT   841 CCCGTTTCTT CTGAACACCT TGCCTTTATG TGTACCTTTA TGGCCTTGTT TATGTGGGGT
         L   A   A   W   C   Y   C   V   A   M   V   C   F   A   A   G   F   M   S   R
CO   901 CTCGCAGCGT GGTGTTATTG TGTGGCGATG GTCTGTTTCG CAGCAGGTTT CATGTCCAGG
WT   901 CTTGCTGCTT GGTGCTATTG TGTGGCCATG GTCTGCTTTG CTGCTGGTTT CATGTCTCGT
         A   P   I   Q   F   K   L   G   W   F   A   F   I   F   P   V   V   G   F   V
CO   961 GCACCTATCC AGTTCAAGTT GGGATGGTTC GCGGTTCATCT TCCCTGTCGT GGGCTTCGTG
WT   961 GCTCCTATTC AATTCAAACT CGGCTGGTTC GCATTTATTT TCCCAGTCGT TGGTTTTGTC
         N   V   T   M   K   I   G   E   M   I   D   S   A   A   F   K   I   F   G   H
CO  1021 AACGTCACCA TGAAGATCGG CGAGATGATT GACTCGGCAG CCTTCAAAAT CTTCGGCCAC
WT  1021 AACGTTACTA TGAAGATTGG TGAGATGATT GATTCGGCCG CGTTCAAGAT CTTTGGTCAT
```

Fig. 4A

```
         V  I  G  A     M  L  A     I  Q  W     M  F  V  M     F  F  M     V  R  A
CO  1081 GTCATCGGAG CCATGTTGGC CATCCAGTGG ATGTTCGTGA TGTTCTTCAT GGTGCGAGCG
WT  1081 GTCATTGGTG CAATGCTTGC CATTCAGTGG ATGTTTGTGA TGTTCTTCAT GGTCCGCGCC
         V  L  L  Q     E  I  M     Y  P  G     R  D  E  D     V  K  T     P  P  G
CO  1141 GTCTTGTTGC AGGAAATCAT GTATCCTGGA CGGGACGAGG ACGTCAAAAC ACCGCCTGGA
WT  1141 GTCTTACTGC AAGAGATCAT GTACCCGGGC CGCGACGAAG ATGTCAAGAC ACCTCCCGGT
         A  T  P  P     P  T  L     V  T  S     P  L  S  F     A  S  L     Q  D  V
CO  1201 GCCACACCTC CTCCGACCCT CGTGACCTCC CCTCTCTCCT TCGCATCCCT CCAGGATGTC
WT  1201 GCCACTCCTC CTCCCACTTT GGTGACGAGT CCCTTGTCCT TTGCTTCGCT GCAAGACGTA
         K  D  G  H     P  I  Q     V  T  V     S  R  T  R     D  R  S     K  Q  H
CO  1261 AAGGATGGAC ACCCCATCCA GGTGACGGTC TCCCGCACTA GGGATCGGTC GAAACAGCAC
WT  1261 AAAGATGGCC ATCCCATTCA GGTCACCGTG TCCCGCACTC GAGACAGAAG CAAACAGCAC
         M  S  Q  G     S  D  E     E  K  I     *
CO  1321 ATGTCCCAGG GCTCGGACGA GGAAAAGATT TAA
WT  1321 ATGTCGCAGG GCTCTGATGA AGAAAAAATC TAG
```

Fig. 4B

SEQUENCE LISTING

<160> NUMBER OF SEQ ID NOS: 5

<210> SEQ ID NO 1
<211> LENGTH: 1353
<212> TYPE: DNA
<213> ORGANISM: Schizosaccharomyces japonicus

<400> SEQUENCE: 1

```
atgtcgtcgg agacaccgac atactcctcc tgggcatccc agaggtacaa cgaattgatt      60
gcatggaacg tcaagggtcc gaggttgccc atcgcacaga ggctcaagca cttcacgtgg     120
tcgtggttca cgtgtactat ggcaacaggc ggtgtcggaa tgatcctcgc gtcgctcccc     180
tataggttca cgggcttgaa caccatcgga aaggtcgtct tcatttttcca ggtggtcttg    240
ttggccatct tctgttcggc catggccttc aggttcattc gctacccgga gactttcaag    300
aagtcgatct atcaccactt ggagaaattg ttcatcggta cattcttgct ctcgatgtcg    360
accttcatcg atatgctcgc agcctacggc tatccttcca ccggtgaatg gatggtgtac    420
ttgatccgaa tcttctactg gatgtacttc gccgtctcct tcgtctacgc gatcttcgca    480
ttcgcaacta ctttccatat gcatccttat accctcgaaa cggcatcgcc tgcctggatc    540
ctcccgattt tccctgcgat gatctccgga gcagtggcag gaaccgtggc attcactcag    600
cctccccatc agctcaaaaa cctcgtggtg tgtggcatta tgttccaggg tttgggcttc    660
tgggtctaca tcatgttgtt cgcggtcaac atgctcaaat tgttcacaaa gggcatgatg    720
ggagcctcgg aacgaccggg tttgttcatg ttcgtcggac ctccggcata cacaggcctc    780
gccctcatcg gtatgggcaa gaccgccatg gattccaaaa tctccatgtt ctccgccact    840
cccgtctcct ccgaacacct cgcattcatg tgtaccttca tggcactctt catgtggggt    900
ctcgcagcgt ggtgttattg tgtggcgatg gtctgtttcg cagcaggttt catgtccagg    960
gcacctatcc agttcaagtt gggatggttc gcgttcatct tccctgtcgt gggcttcgtg   1020
aacgtcacca tgaagatcgg cgagatgatt gactcggcag ccttcaaaat cttcggccac   1080
gtcatcggag ccatgttggc catccagtgg atgttcgtga tgttcttcat ggtgcgagcg   1140
gtcttgttgc aggaaatcat gtatcctgga cgggacgagg acgtcaaaac accgcctgga   1200
gccacacctc ctccgaccct cgtgacctcc cctctctcct tcgcatccct ccaggatgtc   1260
aaggatggac accccatcca ggtgacggtc tcccgcacta gggatcggtc gaaacagcac   1320
atgtcccagg gctcggacga ggaaaagatt taa                                 1353
```

<210> SEQ ID NO 2
<211> LENGTH: 450
<212> TYPE: PRT
<213> ORGANISM: Schizosaccharomyces japonicus

<400> SEQUENCE: 2

Met Ser Ser Glu Thr Pro Thr Tyr Ser Ser Trp Ala Ser Gln Arg Tyr
1               5                   10                  15

Asn Glu Leu Ile Ala Trp Asn Val Lys Gly Pro Arg Leu Pro Ile Ala
            20                  25                  30

Gln Arg Leu Lys His Phe Thr Trp Ser Trp Phe Thr Cys Thr Met Ala
        35                  40                  45

Thr Gly Gly Val Gly Met Ile Leu Ala Ser Leu Pro Tyr Arg Phe Thr
    50                  55                  60

Gly Leu Asn Thr Ile Gly Lys Val Val Phe Ile Phe Gln Val Val Leu
65                  70                  75                  80

Leu Ala Ile Phe Cys Ser Ala Met Ala Phe Arg Phe Ile Arg Tyr Pro
                85                  90                  95

Glu Thr Phe Lys Lys Ser Ile Tyr His His Leu Glu Lys Leu Phe Ile
            100                 105                 110

Gly Thr Phe Leu Leu Ser Met Ser Thr Phe Ile Asp Met Leu Ala Ala
        115                 120                 125

Tyr Gly Tyr Pro Ser Thr Gly Glu Trp Met Val Tyr Leu Ile Arg Ile
    130                 135                 140

Phe Tyr Trp Met Tyr Phe Ala Val Ser Phe Val Tyr Ala Ile Phe Ala
145                 150                 155                 160

Phe Ala Thr Thr Phe His Met His Pro Tyr Thr Leu Glu Thr Ala Ser
                165                 170                 175

Pro Ala Trp Ile Leu Pro Ile Phe Pro Ala Met Ile Ser Gly Ala Val
            180                 185                 190

Ala Gly Thr Val Ala Phe Thr Gln Pro Pro His Gln Leu Lys Asn Leu
        195                 200                 205

Val Val Cys Gly Ile Met Phe Gln Gly Leu Gly Phe Trp Val Tyr Ile
    210                 215                 220

Met Leu Phe Ala Val Asn Met Leu Lys Leu Phe Thr Lys Gly Met Met
225                 230                 235                 240

Gly Ala Ser Glu Arg Pro Gly Leu Phe Met Phe Val Gly Pro Pro Ala
                245                 250                 255

Tyr Thr Gly Leu Ala Leu Ile Gly Met Gly Lys Thr Ala Met Asp Ser
            260                 265                 270

Lys Ile Ser Met Phe Ser Ala Thr Pro Val Ser Ser Glu His Leu Ala
        275                 280                 285

Phe Met Cys Thr Phe Met Ala Leu Phe Met Trp Gly Leu Ala Ala Trp
    290                 295                 300

Cys Tyr Cys Val Ala Met Val Cys Phe Ala Ala Gly Phe Met Ser Arg
305                 310                 315                 320

Ala Pro Ile Gln Phe Lys Leu Gly Trp Phe Ala Phe Ile Phe Pro Val
                325                 330                 335

Val Gly Phe Val Asn Val Thr Met Lys Ile Gly Glu Met Ile Asp Ser
            340                 345                 350

Ala Ala Phe Lys Ile Phe Gly His Val Ile Gly Ala Met Leu Ala Ile
        355                 360                 365

Gln Trp Met Phe Val Met Phe Phe Met Val Arg Ala Val Leu Leu Gln
    370                 375                 380

Glu Ile Met Tyr Pro Gly Arg Asp Glu Asp Val Lys Thr Pro Pro Gly
385                 390                 395                 400

Ala Thr Pro Pro Pro Thr Leu Val Thr Ser Pro Leu Ser Phe Ala Ser
                405                 410                 415

Leu Gln Asp Val Lys Asp Gly His Pro Ile Gln Val Thr Val Ser Arg
            420                 425                 430

Thr Arg Asp Arg Ser Lys Gln His Met Ser Gln Gly Ser Asp Glu Glu
        435                 440                 445

Lys Ile
    450

<210> SEQ ID NO 3
<211> LENGTH: 1353
<212> TYPE: DNA
<213> ORGANISM: Schizosaccharomyces japonicus

<400> SEQUENCE: 3

```
atgtcttcgg aaacgccgac ttacagctct tgggcgagcc aacggtacaa cgaattgatc    60
gcttggaacg tcaagggtcc tcgcttaccc attgcccagc gtctaaaaca cttcacttgg   120
tcctggttta cctgtaccat ggccaccggt ggtgtcggta tgattctggc atcgctgccc   180
taccgattca caggcttaaa cacgattggt aaagtcgtgt tcattttcca ggtcgttttg   240
ctggcgattt tctgttcggc gatggccttt cggttcattc gttacccga aaccttcaaa    300 aagtctattt accatcattt ggagaagctc ttcattggta ccttcctgct ttccatgtcg   360
acgttcatcg atatgctcgc cgcctacgga tacccagca ctggcgagtg gatggtgtac    420
ctaattcgca tttttttactg gatgtacttt gccgtctcgt tcgtatacgc catcttcgca   480
tttgctacca cctttcacat gcatccctac accctggaga cggcttcccc agcatggatt   540
ctgcctattt tcccagctat gattagcggc gctgtcgccg gtactgtggc cttcacacaa   600
ccgccgcacc aattgaagaa tttggtcgtg tgcggtatca tgttccaggg cttgggtttc   660
tgggtgtaca tcatgctgtt cgccgtgaac atgctcaagc tgtttacgaa gggtatgatg   720
ggtgcctctg aacgccctgg tcttttatg ttcgttggtc ctccggccta taccggcttg    780
gctttaatcg gtatgggtaa aactgctatg gactccaaga tctccatgtt ttctgcaacc   840
cccgtttctt ctgaacacct tgcctttatg tgtaccttta tggccttgtt tatgtggggt   900
cttgctgctt ggtgctattg tgtggccatg gtctgctttg ctgctggttt catgtctcgt   960
gctcctattc aattcaaact cggctggttc gcatttattt tcccagtcgt tggttttgtc  1020
aacgttacta tgaagattgg tgagatgatt gattcggccg cgttcaagat ctttggtcat  1080
gtcattggtg caatgcttgc cattcagtgg atgtttgtga tgttcttcat ggtccgcgcc  1140
gtcttactgc aagagatcat gtacccgggc cgcgacgaag atgtcaagac acctcccggt  1200
gccactcctc ctcccacttt ggtgacgagt cccttgtcct ttgcttcgct gcaagacgta  1260
aaagatggcc atcccattca ggtcaccgtg tcccgcactc gagacagaag caaacagcac  1320
atgtcgcagg gctctgatga agaaaaaatc tag                                1353

<210> SEQ ID NO 4
<211> LENGTH: 36
<212> TYPE: DNA
<213> ORGANISM: Schizosaccharomyces japonicus

<400> SEQUENCE: 4
tgtgatagaa catcgtccat aatgtcgtcg gagaca                              36

<210> SEQ ID NO 5
<211> LENGTH: 40
<212> TYPE: DNA
<213> ORGANISM: Schizosaccharomyces japonicus

<400> SEQUENCE: 5
gtgtcagtca cctctagtta ttaaatcttt tcctcgtccg                          40
```

C4 DICARBOXYLIC ACID PRODUCTION IN FILAMENTOUS FUNGI

CROSS-REFERENCE TO RELATED APPLICATIONS

This application is a 35 U.S.C. 371 national application of PCT/US2011/038881, filed on Jun. 2, 2011, which claims priority from U.S. provisional application Ser. No. 61/351, 425, filed on Jun. 4, 2010. The contents of these applications are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to methods for improving the production of C4 dicarboxylic acids (e.g., malic acid) in filamentous fungi.

2. Description of the Related Art

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4 dicarboxylic acids can also serve as building block compounds for the production of large volume industrial chemicals, such as 1,4-butanediol, tetrahydrofuran, and gamma-butyrolactone. The cost of producing these large volume industrial chemicals by traditional petrochemical routes has increased significantly due to the high cost of petroleum derived building blocks.

Organic acids are produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids such as fumaric acid and malic acid can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While malic acid is produced commercially today by chemical synthesis from petrochemical feedstocks, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering*, 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974 and WO 2009/155382. Improvement of malic acid production by genetic engineering of *Aspergillus* will enable economical commercial malic acid production by fermentation.

Malic acid overproduction in *Aspergillus* spp. occurs under specific culture conditions (aerobic conditions and high C:N ratio; calcium carbonate is also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra). It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). U.S. Provisional Application No. 61/327,224, entitled "Methods for Improving Malic Acid Production in Filamentous Fungi" filed Apr. 23, 2010, the content of which is hereby incorporated by reference in its entirety, describes malic acid production in filamentous fungi.

It would be advantageous in the art to improve C4 dicarboxylic acid production, such as malic acid production, in *Aspergillus* as a result of genetic engineering using recombinant DNA techniques. The present invention provides, inter alia, methods for improving C4 dicarboxylic acid production (e.g., malic acid production).

SUMMARY OF THE INVENTION

The present invention relates to methods of producing C4 dicarboxylic acids (e.g., malic acid). In one aspect, the method comprises (a) cultivating a host cell (e.g., a filamentous fungal host cell) comprising a heterologous polynucleotide encoding a C4 dicarboxylic acid transporter described herein; and (b) recovering the C4 dicarboxylic acid (e.g., malic acid). In another aspect, the method comprises (a) transforming into host cell (e.g., a filamentous fungal host cell) a heterologous polynucleotide encoding a C4 dicarboxylic acid transporter described herein; (b) cultivating the transformed organism in a medium; and (c) recovering the C4 dicarboxylic acid (e.g., malic acid).

The present invention also relates to a host cell (e.g., a filamentous fungal host cell, such as *Aspergillus oryzae*) comprising a polynucleotide described herein wherein the host cell secretes and/or is capable of secreting increased levels of a C4 dicarboxylic acid (e.g., malic acid).

BRIEF DESCRIPTION OF THE FIGURES

FIG. 4 shows the genomic codon-optimized DNA sequence (CO), the deduced amino acid sequence, and the genomic wild-type DNA sequence (WT) of a *Schizosaccharomyces japonicus* C4 dicarboxylic acid transporter gene (SEQ ID NOs: 1, 2, and 3, respectively).

DEFINITIONS

Figure 1:
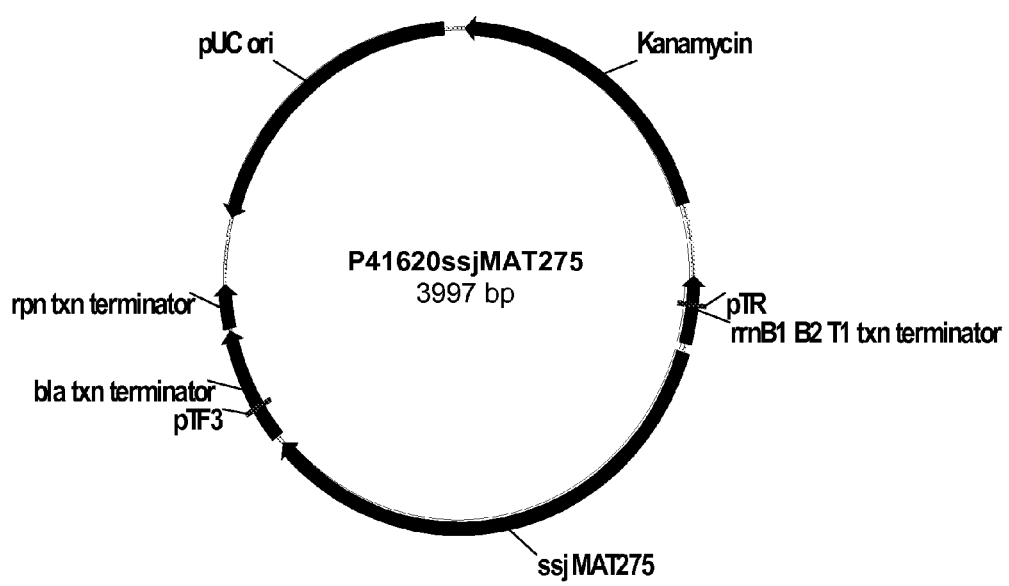
FIG. 1 shows a restriction map of p41620ssjMAT275.

C4 Dicarboxylic Acid Transporter:

The term "C4 dicarboxylic acid transporter" is defined herein as a dicarboxylic acid permease that can transport malic acid, succinic acid, oxaloacetic acid, malonic acid, and/or fumaric acid outside a cell (Grobler et al., 1995, *Yeast* 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786.

The C4 dicarboxylic acid transporters have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the C4 dicarboxylic acid transporter activity (e.g., malic acid transporter activity) of the mature polypeptide of SEQ ID NO: 2.

Malate Dehydrogenase:

The term "malate dehydrogenase" is defined herein as a malate:NAD$^+$ oxidoreductase (EC 1.1.1.37) that catalyzes the reduction of oxaloacetate in the presence of NADH+H$^+$ to malate and NAD$^+$. For purposes of the present invention, malate dehydrogenase activity is determined according to the following procedure. The assay solution consists of 1 mM oxaloacetic acid, 100 mM Tris pH 8.0, 10 mM NaHCO$_3$, 5 mM MgCl$_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malic dehydrogenase (Sigma Chemical Co., St. Louis, Mo., USA) is used as a positive control. One unit of malate dehydrogenase activity equals the amount of enzyme capable of converting 1 pmole of oxaloacetate and NADH+H$^+$ to malate and NAD$^+$ per minute at pH 8.0, 25° C.

Pyruvate Carboxylase:

The term "pyruvate carboxylase" is defined herein as a pyruvate:carbon-dioxide ligase (ADP-forming) (EC 6.4.1.1) that catalyzes the carboxylation of pyruvate in the presence of ATP and HCO$_3^-$ to oxaloacetate, ADP, and phosphate. For purposes of the present invention, pyruvate carboxylase activity is determined according to the procedure of the SIGMA® Quality Control Test procedure for pyruvate carboxylase (Sigma Chemical Co., St. Louis, Mo., USA) except the buffer used in said assay is a Tris buffer at pH 8.0. One unit of pyruvate carboxylase activity equals the amount of enzyme capable of converting 1 µmole of pyruvate and CO$_2$ to oxaloacetate per minute at pH 7.8, 30° C.

Heterologous Polynucleotide:

The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide whose expression is quantitatively altered by the introduction of one or more (e.g., two, several) extra copies of the polynucleotide into the host cell.

Isolated/Purified:

The terms "isolated" and "purified" mean a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97%, at least 98% pure, or at least 99% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97%, at least 98% pure, or at least 99% pure, as determined by agarose electrophoresis.

Mature Polypeptide:

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 90 to 450 of SEQ ID NO: 2 based on the InterProScan program (The European Bioinformatics Institute) that predicts amino acids 1 to 89 of SEQ ID NO: 2 are a signal peptide. In another aspect, the mature polypeptide is amino acids 58 to 450 of SEQ ID NO: 2 based on the SignalP program (Nielsen et al., 1997, *Protein Engineering* 10:1-6) that predicts amino acids 1 to 57 of SEQ ID NO: 2 are a signal peptide.

Mature Polypeptide Coding Sequence:

The term "mature polypeptide coding sequence" means a polynucleotide that encodes a mature polypeptide having C4 dicarboxylic acid transporter activity. The mature polypeptide coding sequence may be from genomic DNA ("mature polypeptide genomic coding sequence") or from cDNA ("mature polypeptide cDNA coding sequence"). In one aspect, the mature polypeptide coding sequence is nucleotides 268 to 1353 of SEQ ID NO: 1 or SEQ ID NO: 3 based on the InterProScan program (The European Bioinformatics Institute) that predicts nucleotides 1 to 267 of SEQ ID NO: 1 encode a signal peptide. In another aspect, the mature polypeptide coding sequence is nucleotides 172 to 1353 of SEQ ID NO: 1 or SEQ ID NO: 3 based on the SignalP program (Nielsen et al., 1997, *Protein Engineering* 10:1-6) that predicts nucleotides 1 to 171 of SEQ ID NO: 1 encode a signal peptide.

Sequence Identity:

The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment:

The term "fragment" means a polypeptide having one or more (e.g., two, several) amino acids deleted from the amino and/or carboxyl terminus of a mature polypeptide. In one aspect, the fragment has C4 dicarboxylic acid transporter activity. In another aspect, a fragment contains at least 385 amino acid residues, e.g., at least 405 amino acid residues or at least 425 amino acid residues of SEQ ID NO: 2.

Subsequence:

The term "subsequence" means a polynucleotide having one or more (e.g., two, several) nucleotides deleted from the 5' and/or 3' end of a mature polypeptide coding sequence. In one aspect, the subsequence encodes a fragment having C4 dicarboxylic acid transporter activity. In another aspect, a subsequence contains at least 1155 nucleotides, e.g., at least 1215 nucleotides or at least 1275 nucleotides of SEQ ID NO: 1 or SEQ ID NO: 3.

Allelic Variant:

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding Sequence:

The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be genomic DNA, cDNA, a synthetic polynucleotide, and/or a recombinant polynucleotide.

cDNA:

The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA. In some instances, a cDNA sequence may be identical to a genomic DNA sequence.

Nucleic Acid Construct:

The term "nucleic acid construct" means a nucleic acid molecule, either single-stranded or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control Sequences:

The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably Linked:

The term "operably linked" means a configuration in which a control sequence is placed at an appropriate position relative to the coding sequence of a polynucleotide such that the control sequence directs the expression of the coding sequence.

Expression:

The term "expression" includes any step involved in the production of the polypeptide including, but not limited to, transcription, post-transcriptional modification, translation, post-translational modification, and secretion.

Expression Vector:

The term "expression vector" means a linear or circular DNA molecule that comprises a polynucleotide encoding a polypeptide and is operably linked to additional nucleotides that provide for its expression.

Host Cell:

The term "host cell" means any cell type that is susceptible to transformation, transfection, transduction, and the like with a nucleic acid construct or expression vector comprising a polynucleotide of the present invention (e.g., a polynucleotide encoding a C4 dicarboxylic acid transporter). The term "host cell" encompasses any progeny of a parent cell that is not identical to the parent cell due to mutations that occur during replication.

Variant:

The term "variant" means a polypeptide having activity, e.g., C4 dicarboxylic acid transporter activity, comprising an alteration, i.e., a substitution, insertion, and/or deletion of one or more (e.g., two, several) amino acid residues at one or more positions. A substitution means a replacement of an amino acid occupying a position with a different amino acid; a deletion means removal of an amino acid occupying a position; and an insertion means adding one or more, e.g., 1-3 amino acids, adjacent to an amino acid occupying a position.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention describes the overexpression of specific genes in a host cell, such as a filamentous fungus, e.g., *Aspergillus*, to enhance the production of C4 dicarboxylic acids, (e.g., malic acid) that encompasses transport of the C4 dicarboxylic acid out of the cell via a C4 dicarboxylic acid transporter. In the present invention, the C4 dicarboxylic acid transporter can be any described C4 dicarboxylic acid transporter that is suitable for practicing the present invention. In one aspect, the C4 dicarboxylic acid transporter is a transporter that is overexpressed under culture conditions that produces C4 dicarboxylic acid in high titers.

In one aspect, the present invention relates to methods of producing a C4 dicarboxylic acid (e.g., malic acid), comprising: (a) cultivating a host cell (e.g., a filamentous fungal host cell) comprising a heterologous polynucleotide encoding a C4 dicarboxylic acid transporter, wherein the host cell secretes increased levels of the malic acid compared to the host cell without the heterologous polynucleotide encoding the C4 dicarboxylic acid transporter and wherein the transporter is selected from: (i) a C4 dicarboxylic acid transporter having at least 60% sequence identity to the mature polypeptide of SEQ ID NO: 2; (ii) a C4 dicarboxylic acid transporter encoded by a polynucleotide that hybridizes under low stringency conditions with the mature polypeptide coding sequence of SEQ ID NO: 1 or SEQ ID NO: 3, or the full-length complementary strand thereof; (iii) a C4 dicarboxylic acid transporter encoded by a polynucleotide having at least 60% sequence identity to the mature polypeptide coding sequence of SEQ ID NO: 1 or SEQ ID NO: 3; (iv) a C4 dicarboxylic acid transporter variant comprising a substitution, deletion, and/or insertion of one or more (e.g., two, several) amino acids of the mature polypeptide of SEQ ID NO: 2; and (v) a fragment of the C4 dicarboxylic acid transporter of (i), (ii), (iii), or (iv) that has C4 dicarboxylic acid transporter activity; and (b) recovering the C4 dicarboxylic acid.

In another aspect, the present invention relates to methods for increasing C4 dicarboxylic acid (e.g., malic acid) production, comprising: (a) transforming into a host cell (e.g., a filamentous fungal host cell) a heterologous polynucleotide encoding a C4 dicarboxylic acid transporter, wherein the host cell secretes increased levels of the malic acid compared to the host cell without the heterologous polynucleotide encoding the C4 dicarboxylic acid transporter and wherein the transporter is selected from: (i) a C4 dicarboxylic acid transporter having at least 60% sequence identity to the mature polypeptide of SEQ ID NO: 2; (ii) a C4 dicarboxylic acid transporter encoded by a polynucleotide that hybridizes under low stringency conditions with the mature polypeptide coding sequence of SEQ ID NO: 1 or SEQ ID NO: 3, or the full-length complementary strand thereof; (iii) a C4 dicarboxylic acid transporter encoded by a polynucleotide having at least 60% sequence identity to the mature polypeptide coding sequence of SEQ ID NO: 1 or SEQ ID NO: 3; (iv) a C4 dicarboxylic acid transporter variant comprising a substitution, deletion, and/or insertion of one or more (e.g., two, several) amino acids of the mature polypeptide of SEQ ID NO: 2; and (v) a fragment of the C4 dicarboxylic acid transporter of (i), (ii), (iii), or (iv) that has C4 dicarboxylic acid transporter activity; and (b) cultivating the transformed organism in a medium; and (c) recovering the C4 dicarboxylic acid.

In some of these aspects, the C4 dicarboxylic acid is malic acid, succinic acid, oxaloacetic acid, malonic acid, or fumaric acid, or combinations thereof. In some aspects, the C4 dicarboxylic acid is malic acid, succinic acid, or fumaric acid, or combinations thereof. In some aspects, the C4 dicarboxylic acid is malic acid or fumaric acid, or a combination of malic acid and fumaric acid. In some aspects, the C4 dicarboxylic acid is malic acid.

In any of these aspects, the C4 dicarboxylic acid transporter has C4 dicarboxylic acid transporter activity and comprises an amino acid sequence having a degree of sequence identity to SEQ ID NO: 2 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one aspect, the C4 dicarboxylic acid transporter differs by no more than, for example, ten amino acids, e.g., by no more than five amino acids, by no more than four amino acids, by no more than three amino acids, by no more than two amino acids, or by no more than one amino acid from the mature polypeptide of SEQ ID NO: 2, as described in the discussion below on variants.

In one aspect, the C4 dicarboxylic acid transporter comprises the amino acid sequence of SEQ ID NO: 2 or an allelic variant thereof; or a fragment of the foregoing, having C4 dicarboxylic acid transporter activity. In another aspect, the C4 dicarboxylic acid transporter comprises the amino acid sequence of SEQ ID NO: 2. In another aspect, the C4 dicarboxylic acid transporter may comprise or consist of the amino acid sequence of SEQ ID NO: 2 or an allelic variant thereof; or a fragment thereof having C4 dicarboxylic acid transporter activity. In another aspect, the C4 dicarboxylic acid transporter comprises or consists of the mature polypeptide of SEQ ID NO: 2. In another aspect, the C4 dicarboxylic acid transporter comprises or consists of amino acids 58 to 450 of SEQ ID NO: 2. In another aspect, the C4 dicarboxylic acid transporter comprises or consists of amino acids 90 to 450 of SEQ ID NO: 2.

In any of these aspects, the C4 dicarboxylic acid transporter is encoded by a polynucleotide as described below in the section on isolated polynucleotides.

In any of these aspects, the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1 and/or SEQ ID NO: 3, or the full-length complementary strand thereof.

In one aspect, the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1, or the full-length complementary strand thereof.

In another aspect, the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 3, or the full-length complementary strand thereof.

The polynucleotide of SEQ ID NO: 1, SEQ ID NO: 3, or a subsequence thereof; as well as the amino acid sequence of SEQ ID NO: 2; or a fragment thereof; may be used to design nucleic acid probes to identify and clone DNA encoding C4 dicarboxylic acid transporters from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, e.g., at least 14, at least 25, at least 35, or at least 70 nucleotides in length. It is preferred that the nucleic acid probe is at least 100 nucleotides in length. For example, the nucleic acid probe may be at least 200 nucleotides, e.g., at least 300 nucleotides, at least 400 nucleotides, or at least 500 nucleotides in length. Even longer probes may be used, e.g., nucleic acid probes that are at least 600 nucleotides, e.g., at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having C4 dicarboxylic acid transporter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, or a subsequence thereof, the carrier material may be used in a Southern blot.

For purposes of the present invention, hybridization indicates that the polynucleotide hybridizes to a labeled nucleic acid probe corresponding to the mature polypeptide coding sequence of SEQ ID NO: 1, SEQ ID NO: 3, or the full-length complementary strand thereof; or a subsequence of the foregoing; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1 or SEQ ID NO: 3. In another aspect, the nucleic acid probe is the mature polypeptide coding sequence of SEQ ID NO: 1. In another aspect, the nucleic acid probe is the mature polypeptide coding sequence of SEQ ID NO: 3. In another aspect, the nucleic acid probe is a polynucleotide that encodes the polypeptide of SEQ ID NO: 2, or a fragment thereof. In another aspect, the nucleic acid probe is SEQ ID NO: 1. In another aspect, the nucleic acid probe is SEQ ID NO: 3.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In any aspect of the methods, the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3. In one aspect of the methods, the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1. In another aspect of the methods, the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 3.

In any of these aspects, the C4 dicarboxylic acid transporter is a variant comprising a substitution, deletion, and/or insertion of one or more (e.g., two, several) amino acids of the mature polypeptide of SEQ ID NO: 2. Preferably, amino acid changes are of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for C4 dicarboxylic acid transporter activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of the mature polypeptide of SEQ ID NO: 2 is not more than 10, e.g., not more than 1, 2, 3, 4, 5, 6, 7, 8 or 9.

In another aspect, the C4 dicarboxylic acid transporter is a fragment of SEQ ID NO: 2, wherein the fragment has C4 dicarboxylic acid transporter activity. In one aspect, the fragment contains at least 385 amino acid residues, e.g., at least 405 amino acid residues, or at least 425 amino acid residues of SEQ ID NO: 2.

The C4 dicarboxylic acid transporter may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

Techniques used to isolate or clone a polynucleotide encoding a C4 dicarboxylic acid transporter used in any of the aspects mentioned herein (e.g., any aspect of SEQ ID NO: 2 for a method of producing a C4 dicarboxylic acid, method of increasing C4 dicarboxylic acid production, or host cell thereof) are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shares structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Schizosaccharomyces*, or another or related organism and thus, for example, may be an allelic or species variant of the polypeptide encoding region of the nucleotide sequence of SEQ ID NO 1 or SEQ ID NO: 3.

In one aspect, the isolated polynucleotide comprises or consists of SEQ ID NO: 1 or SEQ ID NO: 3. In another aspect, the isolated polynucleotide encodes a C4 dicarboxylic acid transporter comprising or consisting of SEQ ID NO: 2. The present invention also encompasses nucleotide sequences that encode polypeptides comprising or consisting of the amino acid sequence of SEQ ID NO: 2 (or any of the related aspects thereof), which differ from SEQ ID NO: 1 or SEQ ID NO: 3 by virtue of the degeneracy of the genetic code. The present invention also relates to subsequences of SEQ ID NO: 1 that encode fragments of SEQ ID NO: 2 that have C4 dicarboxylic acid transporter activity.

In another aspect, the isolated polynucleotide can be a mutant polynucleotide comprising or consisting of at least one mutation in SEQ ID NO: 1 or SEQ ID NO: 3, in which the mutant nucleotide sequence encodes SEQ ID NO: 2.

In another aspect, the isolated polynucleotide encoding a C4 dicarboxylic acid transporter hybridizes under very low stringency conditions, low stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof. In one aspect, the isolated polynucleotide encoding a C4 dicarboxylic acid transporter hybridizes under very low stringency conditions, low stringency conditions, medium stringency conditions, medium-high stringency conditions, high stringency conditions, or very high stringency conditions with the mature polypeptide coding sequence of SEQ ID NO: 1, or the full-length complementary strand thereof. In another aspect, the isolated polynucleotide encoding a C4 dicarboxylic acid transporter hybridizes under very low stringency conditions, low stringency conditions, medium stringency conditions, medium-high stringency conditions, high stringency conditions, or very high stringency conditions with the mature polypeptide coding sequence of SEQ ID NO: 3, or the full-length complementary strand thereof.

In another aspect, the isolated polynucleotide comprises or consists of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO:3 which encodes a polypeptide having C4 dicarboxylic acid transporter activity. In one aspect, the isolated polynucleotide comprises or consists of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 which encodes a polypeptide having C4 dicarboxylic acid transporter activity. In another aspect, the isolated polynucleotide comprises or consists of a nucleotide sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 which encodes a polypeptide having C4 dicarboxylic acid transporter activity.

In another aspect, the isolated polynucleotide encoding a C4 dicarboxylic acid transporter having C4 dicarboxylic acid transporter activity is obtained by (a) hybridizing a population of DNA under very low, low, medium, medium-high, high, or very high stringency conditions with the mature polypeptide coding sequence of SEQ ID NO: 1 or SEQ ID NO: 3, or the full-length complementary strand thereof; and (b) isolating the hybridizing polynucleotide.

Sources of C4 Dicarboxylic Acid Transporters

The C4 dicarboxylic acid transporter may be obtained from microorganisms of any genus. For purposes of the present invention, the term "obtained from" as used herein in connection with a given source shall mean that the C4 dicarboxylic acid transporter encoded by a polynucleotide is produced by the source or by a cell in which the polynucleotide from the source has been inserted. In one aspect, the C4 dicarboxylic acid transporter is transported to the outer membrane.

The C4 dicarboxylic acid transporter may be a bacterial C4 dicarboxylic acid transporter. For example, the C4 dicarboxylic acid transporter may be a Gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* C4 dicarboxylic acid transporter, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* C4 dicarboxylic acid transporter.

In one aspect, the C4 dicarboxylic acid transporter is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* C4 dicarboxylic acid transporter.

In another aspect, the C4 dicarboxylic acid transporter is a *Streptococcus equisimilis, Streptococcus pyogenes, Streptococcus uberis,* or *Streptococcus equi* subsp. *Zooepidemicus* C4 dicarboxylic acid transporter.

In another aspect, the C4 dicarboxylic acid transporter is a *Streptomyces achromogenes, Streptomyces avermitilis, Streptomyces coelicolor, Streptomyces griseus,* or *Streptomyces lividans* C4 dicarboxylic acid transporter.

The C4 dicarboxylic acid transporter may be a fungal C4 dicarboxylic acid transporter. In one aspect, the fungal C4 dicarboxylic acid transporter is a yeast C4 dicarboxylic acid transporter such as a *Candida, Kluyveromyces, Pichia, Saccharomyces, Schizosaccharomyces,* or *Yarrowia* C4 dicarboxylic acid transporter.

In another aspect, the C4 dicarboxylic acid transporter is a *Schizosaccharomyces* C4 dicarboxylic acid transporter, such as a *Schizosaccharomyces japonicus* C4 dicarboxylic acid transporter. In one aspect, the C4 dicarboxylic acid transporter a *Schizosaccharomyces japonicus* C4 dicarboxylic acid transporter of SEQ ID NO: 2.

In another aspect, the fungal C4 dicarboxylic acid transporter is a filamentous fungal C4 dicarboxylic acid transporter such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* C4 dicarboxylic acid transporter.

In another aspect, the C4 dicarboxylic acid transporter is a *Saccharomyces carlsbergensis, Saccharomyces cerevisiae, Saccharomyces diastaticus, Saccharomyces douglasfi, Saccharomyces kluyveri, Saccharomyces norbensis,* or *Saccharomyces oviformis* C4 dicarboxylic acid transporter.

In another aspect, the C4 dicarboxylic acid transporter is an *Acremonium cellulolyticus, Aspergillus aculeatus, Aspergillus awamori, Aspergillus flavus, Aspergillus fumigatus, Aspergillus foetidus, Aspergillus japonicus, Aspergillus nidulans, Aspergillus niger, Aspergillus oryzae, Aspergillus sojae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermo-* phila, *Thielavia terrestris, Trichoderma harzianum, Trichoderma koningii, Trichoderma longibrachiatum, Trichoderma reesei,* or *Trichoderma viride* C4 dicarboxylic acid transporter.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The C4 dicarboxylic acid transporter may also be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding a C4 dicarboxylic acid transporter may then be derived by similarly screening a genomic or cDNA library of another microorganism or mixed DNA sample. Once a polynucleotide encoding a C4 dicarboxylic acid transporter has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual,* 2d edition, Cold Spring Harbor, N.Y.).

Nucleic Acid Constructs

The present invention also relates to nucleic acid constructs comprising a polynucleotide encoding a C4 dicarboxylic acid transporter (or other polynucleotides described herein, such as a polynucleotide encoding a malate dehydrogenase and/or a pyruvate carboxylase) linked to one or more (e.g., two, several) control sequences that direct the expression of the coding sequence in a suitable host cell under conditions compatible with the control sequences. In one aspect, the heterologous polynucleotide encoding a C4 dicarboxylic acid transporter is operably linked to promoter foreign to the polynucleotide. In one aspect, a second heterologous polynucleotide encoding a malate dehydrogenase is operably linked to promoter foreign to the polynucleotide. In one aspect, a third heterologous polynucleotide encoding a pyruvate carboxylase is operably linked to promoter foreign to the polynucleotide.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a C4 dicarboxylic acid transporter or other polynucleotides described herein, such as a polynucleotide encoding a malate dehydrogenase and/or a pyruvate carboxylase). The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide encoding a C4 dicarboxylic acid transporter (or other polynucleotides described herein, such as a polynucleotide encoding a malate dehydrogenase and/or a pyruvate carboxylase), a promoter, and transcriptional and translational stop signals. The various nucleotide and control sequences may be joined together to produce a recombinant expression vector that may include one or more (e.g., two, several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector may contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide described herein (e.g., a polynucleotide encoding a C4 dicarboxylic acid transporter, a malate dehydrogenase, and/or a pyruvate carboxylase) operably linked to one or more (e.g., two, several) control sequences that direct the production of a polypeptides described herein. A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. In some cases, the choice of a host cell depends upon the gene encoding the polypeptide and its source. The aspects described below apply to the host cells, per se, as well as methods using the host cells.

The host cell may be any cell capable of the recombinant production of a polypeptide of the present invention, e.g., a prokaryote or a eukaryote, and/or any cell (e.g., any filamentous fungal cell) capable of the recombinant production of a C4 dicarboxylic acid (e.g., malic acid).

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In one aspect, the host cell is an *Aspergillus* host cell. In another aspect, the host cell is *Aspergillus oryzae.*

Fungal cells may be transformed by a process involving protoplast formation, transformation of the protoplasts, and regeneration of the cell wall in a manner known per se.

Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises a polynucleotide encoding a C4 dicarboxylic acid transporter and is capable of producing a C4 dicarboxylic acid (e.g., malic acid) as described in the methods herein. In one aspect, the host cell (e.g., a filamentous fungal host cell), comprises a heterologous polynucleotide encoding a C4 dicarboxylic acid transporter described herein, wherein the host cell secretes and/or is capable of secreting an increased level of a C4 dicarboxylic acid (e.g., malic acid) compared to the filamentous fungal host cell without the C4 dicarboxylic acid transporter when cultivated under the same conditions.

In one aspect, the host cell comprises a heterologous polynucleotide encoding a C4 dicarboxylic acid transporter described herein (e.g., SEQ ID NO: 1, SEQ ID NO: 3, or any described aspect thereof) and a heterologous polynucleotide encoding a malate dehydrogenase. In the present invention, the malate dehydrogenase can be any malate dehydrogenase that is suitable for practicing the present invention. In particular, the malate dehydrogenase is may be an enzyme that is present in the cytosol of the host cell.

Malate dehydrogenases that can be used to practice the present invention include, but are not limited to, an *Aspergillus fumigatus* malate dehydrogenase (AFUA_2G13800; Nierman et al., 2005, *Nature* 438: 1151-1156); *Aspergillus nidulans* malate dehydrogenase (AN5031.1, AN6499.1; Sims et al., 2004, *Mycol. Res.* 108: 853-857); *Aspergillus niger* malate dehydrogenase (An11g07190, An12g00160, An15g00070; Pel et al., 2007, *Nature Biotechnology* 25: 221-231); *Aspergillus oryzae* NRRL 3488 malate dehydrogenase (genomic DNA sequence of SEQ ID NO: 19 and the deduced amino acid sequence of SEQ ID NO: 20); *Phytophthora infestans* malate dehydrogenase (PITG 15476.1; Calcagno et al., 2009, *Mycological Research* 113: 771-781); and *Saccharomyces cerevisiae* malate dehydrogenase (YOL126C; Minard and McAlister-Henn, 1991, *Mol. Cell. Biol.* 11: 370-380; YDL078C; McAlister-Henn et al., 1995, *Journal of Biological Chemistry* 270: 21220-21225).

The malate dehydrogenase may be obtained from microorganisms of any genus. For purposes of the present invention, the term "obtained from" as used herein in connection with a given source shall mean that the malate dehydrogenase encoded by a polynucleotide is produced by the source or by a cell in which the polynucleotide from the source has been inserted. In one aspect, the malate dehydrogenase may be a bacterial, yeast, or filamentous fungal malate dehydrogenase obtained from the microorganisms described herein. In another aspect, the malate dehydrogenase is an *Aspergillus oryzae* malate dehydrogenase.

The malate dehydrogenase may also be identified and obtained from other sources including microorganisms isolated from nature (e.g., soil, composts, water, etc.) or DNA samples obtained directly from natural materials (e.g., soil, composts, water, etc,) as described supra. The malate dehydrogenase can also include fused polypeptides or cleavable fusion polypeptides, as described supra. In one aspect, the malate dehydrogenase is a variant of a parent malate dehydrogenase that comprises one or more (e.g., two, several) modifications of the amino acid sequence, which reduces mitochondrial import in vivo of the malate dehydrogenase. Techniques used to isolate or clone a polynucleotide encoding a malate dehydrogenase are described supra.

In another aspect, the host cell comprises a heterologous polynucleotide encoding a C4 dicarboxylic acid transporter described herein (e.g., SEQ ID NO: 1, SEQ ID NO: 3, or any described aspect thereof) and a heterologous polynucleotide encoding a pyruvate carboxylase. In the present invention, the pyruvate carboxylase can be any pyruvate carboxylase that is suitable for practicing the present invention. In particular, the pyruvate carboxylase is may be an enzyme that is present in the cytosol of the host cell.

Pyruvate carboxylases that can be used to practice the present invention include, but are not limited to, a *Aspergillus clavatus* NRRL 1 pyruvate carboxylase (XP_001271664; Direct Submission, Submitted (26-OCT-2006), The Institute for Genomic Research, 9712 Medical Center Drive, Rockville, Md. 20850, USA); *Aspergillus fumigatus* Af293 pyruvate carboxylase (XP_752054; Nierman et al., 2005, *Nature* 438: 1151-1156); *Aspergillus nidulans* FGSC A4 pyruvate carboxylase (XP_662066; Galagan et al., 2005, *Nature* 438: 1105-1115); *Aspergillus niger* pyruvate carboxylase (An15g02820; Pel et al., 2007, *Nature Biotechnology* 25: 221-231; ASPNG 5061; Panneman et al., Submitted (JUL-1998) to the EMBL/GenBank/DDBJ databases); *Aspergillus terreus* pyruvate carboxylase (O93918; Direct Submission, Submitted (October 1998) The Institute for Genomic Research, 9712 Medical Center Drive, Rockville, Md. 20850, USA); *Magnaporthe grisea* 70-15 pyruvate carboxylase (XP_367852; Direct Submission, Submitted (26 Sep. 2005) Broad Institute of MIT and Harvard, 320 Charles Street, Cambridge, Mass. 02142, USA); *Neurospora crassa* OR74A pyruvate carboxylase (XP_965636; Galagan et al., 2003, *Nature* 422: 859-868); *Rhizopus oryzae* pyruvate carboxylase (RO3G_06931.1); *Saccharomyces cerevisiae* pyruvate carboxylase (NP_009777; Gaffeau et al., 1996, *Science* 274: 546-547); *Schizosaccharomyces pombe* pyruvate carboxylase (NP_595900; Direct Submission, Submitted (29 Jun. 2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87).

The pyruvate carboxylases may be obtained from microorganisms of any genus. For purposes of the present invention, the term "obtained from" as used herein in connection with a given source shall mean that the pyruvate carboxylase encoded by a polynucleotide is produced by the source or by a cell in which the polynucleotide from the source has been inserted. In one aspect, the pyruvate carboxylase may be a bacterial, a yeast, or a filamentous fungal pyruvate carboxylase obtained from the microorganisms described herein. In another aspect, the pyruvate carboxylase is an *Aspergillus oryzae* pyruvate carboxylase.

The pyruvate carboxylase may also be identified and obtained from other sources including microorganisms isolated from nature (e.g., soil, composts, water, etc.) or DNA samples obtained directly from natural materials (e.g., soil, composts, water, etc,) as described supra. The pyruvate carboxylase can also include fused polypeptides or cleavable fusion polypeptides, as described supra. The pyruvate carboxylase can also be a variant of a mitochondrial pyruvate carboxylase, such that in vivo importation into the mitochondria is reduced thereby increasing the level of the pyruvate carboxylase variant in the cytosol. Techniques used to isolate or clone a polynucleotide encoding a pyruvate carboxylase are described supra.

In another aspect, the host cell comprises a heterologous polynucleotide encoding a C4 dicarboxylic acid transporter described herein (e.g., SEQ ID NO: 1, SEQ ID NO: 3, or any described aspect thereof), a heterologous polynucleotide encoding a malate dehydrogenase, and a heterologous polynucleotide encoding a pyruvate carboxylase. Examples of malate dehydrogenases and pyruvate carboxylases that may be used with these hosts cells can be found, for example, in U.S. Provisional Patent Application No. 61/327,224, entitled "Methods for Improving Malic Acid Production in Filamentous Fungi" filed Apr. 23, 2010, the content of which is hereby incorporated by reference in its entirety, particularly with respect to the polynucleotides encoding malate dehydrogenase and pyruvate carboxylase polypeptides described therein. In any of these aspects, the heterologous polynucleotides may be operably linked to a foreign promoter, as described supra.

In any of these aspects, the host cell secretes and/or is capable of secreting an increased level of C4 dicarboxylic acid (e.g., malic acid) of at least 25%, e.g., at least 50%, at least 100%, at least 150%, at least 200%, at least 300%, or at 500% compared to the host cell without the polynucleotide encoding the heterologous polynucleotide encoding a C4 dicarboxylic acid transporter when cultivated under the same conditions. The recombinant filamentous fungal host cells may be cultivated in a nutrient medium suitable for production of the C4 dicarboxylic acid transporter, the malate dehydrogenase, and/or the pyruvate carboxylase using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers, may be prepared according to published compositions (e.g., in catalogues of the American Type Culture Collection), or may be prepared from commercially available ingredients.

The C4 dicarboxylic acid transporter, malate dehydrogenase, and pyruvate carboxylase can be detected using methods known in the art that are specific for the polypeptides. These detection methods may include use of specific antibodies, formation of an enzyme product, or disappearance of an enzyme substrate. For example, an enzyme assay may be used to determine the activity of the malate dehydrogenase variant and the pyruvate carboxylase, as described herein. Malic acid can be recovered using any method known in the art. See, for example, WO 1998/022611 and U.S. Pat. No. 7,601,865.

The present invention is further described by the following examples that should not be construed as limiting the scope of the invention.

EXAMPLES

Chemicals used as buffers and substrates were commercial products of at least reagent grade.
Strains
*Schizosaccharomyces japonicus* was used as source of the C4 dicarboxylic acid transporter gene ssjMAT275 (NCBI GeneID: 7048154). *Aspergillus oryzae* NRRL 3488 (or ATCC 56747) was used for production of the C4 dicarboxylic acids.
Media
YEG medium was composed of 20g glucose, 5g yeast extract, and deionized water to 1 liter.
COVE plates were composed of 1 M sucrose, 2% COVE salt solution, 10 mM acetamide, 15 mM CsCl, and 25 g/L Agar Noble.
COVE salt solution was composed of 26g KCl, 26g $MgSO_4 \cdot 7H_2O$, 76g $KH_2PO_4$, 50 mL of COVE trace elements solution, and deionized water to 1 liter.

COVE trace elements solution was composed of 0.04 g $Na_2B_4O_7 \cdot 10H_2O$, 0.04 g $CuSO_4 \cdot 5H_2O$, 1.2 g $FeSO_4 \cdot 7H_2O$, 0.7 g $MnSO_4 \cdot H_2O$, 0.8 g $Na_2MoO_2 \cdot 2H_2O$, 10g $ZnSO_4 \cdot 7H_2O$ and deionized water to 1 liter.

Seed medium B is composed of 30g glucose, 3g Bacto Peptone, 560 mg $KH_2PO_4$, 560 mg $K_2HPO_4$, 925 mg $NaH_2PO_4 \cdot H_2O$, 820 mg $Na_2HPO_4$, 75 mg $MgSO_4 \cdot 7H_2O$, 75 mg $CaCl_2 \cdot H_2O$, 0.75 mL of 1000× Micronutrient Solution, and deionized water to 1 liter.

Acid production medium C is composed of 100g glucose, 80g $CaCO_3$, 6g Bacto Peptone, 150 mg $KH_2PO_4$, 150 mg $K_2HPO_4$, 100 mg $MgSO_4 \cdot 7H_2O$, 100 mg $CaCl_2 \cdot H_2O$, 1 mL 1000× Micronutrient Solution, and deionized water to 1 liter.

1000× Micronutrient Solution is composed of 5g NaCl, 5g $FeSO_4 \cdot 7H_2O$, 1g citric acid, and deionized water to 1 liter.

PDA plates are composed of 39 g/L potato dextrose agar.
2XYT+amp plates were composed of 16g tryptone, 10g yeast extract, 5g NaCl, 100 mg ampicillin, 15g Bacto agar, and deionized water to 1 liter.

Example 1

Cloning of a *Schizosaccharomyces japonicus* C4 Dicarboxylic Acid Transporter Gene and Construction of Expression Vector pSaMF37

The 1353 by C4 dicarboxylic acid transporter protein gene ssjMAT275 was codon optimized for expression in *A. oryzae* and synthetically constructed into p41620ssjMAT275 (FIG. 1; DNA2.0, Menlo Park, Calif., USA). The ssjMAT275 gene was amplified from p41620ssjMAT275 using primers 069869 and 069870 shown below.

```
Primer 069869:
                                      (SEQ ID NO: 4)
5'-TGTGATAGAACATCGTCCATAATGTCGTCGGAGACA-3'

Primer 069870:
                                      (SEQ ID NO: 5)
5'-GTGTCAGTCACCTCTAGTTATTAAATCTTTTCCTCGTCCG-3'
```

The PCR reaction was composed of 10 µL 5× reaction buffer (Finnzymes, Inc. Massachusetts, USA), 1 µL p41620ssjMAT275 template (20 ng/µL), 1 µL primer 069869 (100 ng/µL), 1 µL primer 069870 (100 ng/µL), 1 µL dNTP mixture (10 mM), 35.5 µL deionized water, and 0.5 µL Phusion™ Hot Start High-Fidelity DNA Polymerase (Finnzymes, Inc. Massachusetts, USA). The amplification reaction was incubated in an EPPENDORF® MASTERCYCLER®(Eppendorf Scientific Inc. Westbury, N.Y., USA) programmed for 1 cycle at 98° C. for 30 seconds; 30 cycles each at 98° C. for 10 seconds, 60° C. for 30 seconds, and 72° C. for 1 minutes; and one cycle at 72° C. for 10 minutes. The PCR reaction was subjected to a restriction digest with DpnI for 1 hour to degrade any plasmid DNA template, then purified using a MinElute® PCR Purification Kit (QIAGEN Inc., Valencia, Calif., USA).

Figure 2:
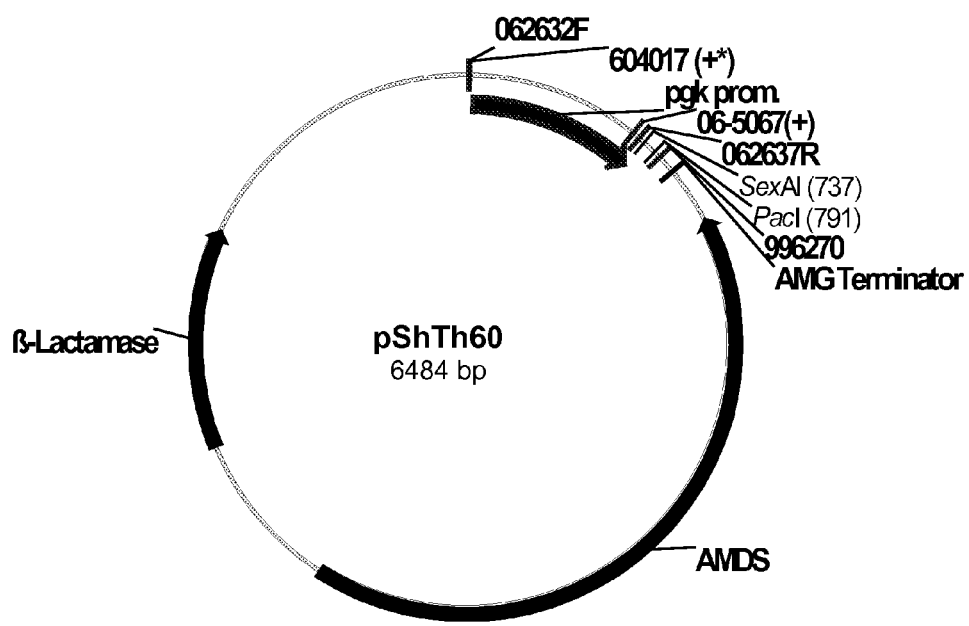
FIG. 2 shows a restriction map of pShTh60.
Figure 3:
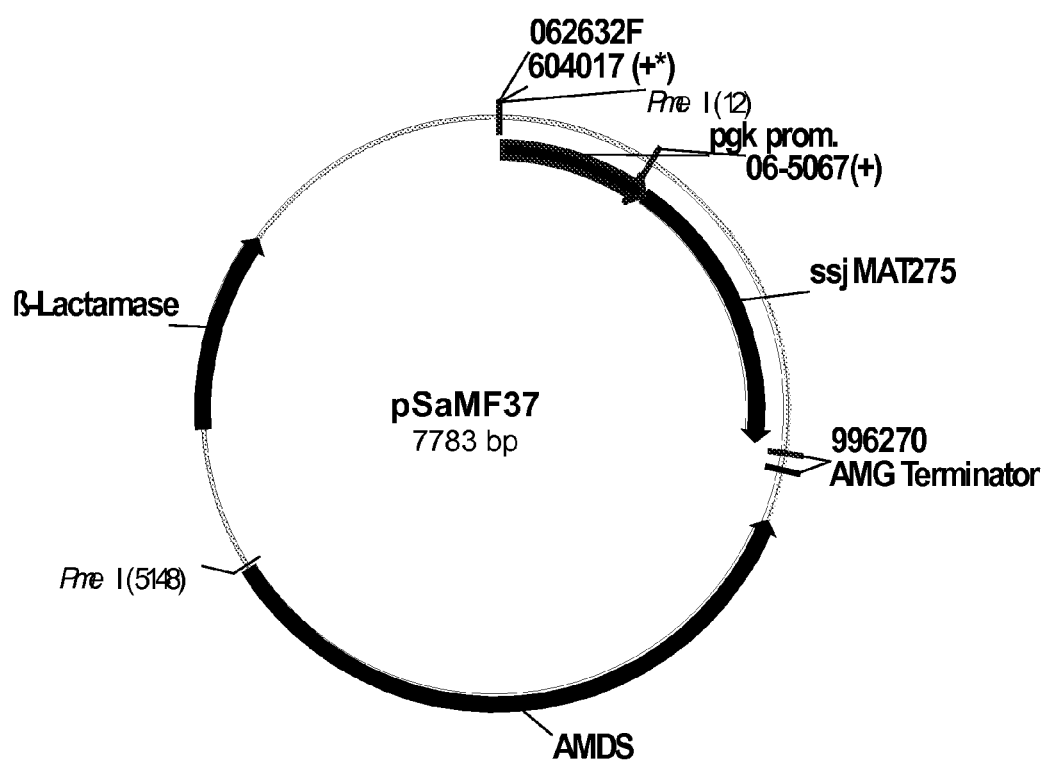
FIG. 3 shows a restriction map of pSaMF37.

Plasmid pShTh60 (FIG. 2; see also U.S. Provisional Application No. 61/327,224, filed Apr. 23, 2010) was digested with SexAI and PacI then separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc., Valencia, Calif., USA). The purified PCR product above was then inserted into the digested pShTh60 using an In-Fusion™ Advantage reaction kit (Clontech, Mountain View, Calif., USA) composed of 2 µL 5× buffer (Clontech, Mountain View, Calif., USA), 0.5 µL purified PCR product (170 ng/µL), 1.5 µL digested and gel-purified pShTh60 (132 ng/µL), 1 µL In-Fusion™ enzyme and 5 µL deionized water. The reaction was incubated at 37° C. for 15 minutes then 50° C. for 15 minutes after which it was placed on ice for 5 minutes and diluted with 40 µL TE buffer (10 mM Tris Base, 1 mM EDTA, pH 8.0) resulting in pSaMF37 (FIG. 3).

A 2.5 µL aliquot of the ligation reaction above was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight. The resulting transformants were picked and subjected to DNA sequencing to confirm that the ssjMAT275 gene was integrated into the vector.

The codon-optimized nucleotide sequence (CO), deduced amino acid sequence, and wild-type nucleotide sequence (WT) of the *Schizosaccharomyces japonicus* ssjMAT275 gene are shown in FIGS. 4A and 4B (SEQ ID NO: 1, SEQ ID NO: 2, and SEQ ID NO: 3, respectively). The coding sequence is 1353 by including the stop codon. The encoded predicted protein is 450 amino acids. Using the SignalP program (Nielsen et al., 1997, *Protein Engineering* 10:1-6), a signal peptide of 57 residues was predicted. Based on this program, the predicted mature protein contains 393 amino acids with a predicted molecular mass of 44.1 kDa and an isoelectric pH of 9.03. Using the InterProScan program (The European Bioinformatics Institute), a signal peptide of 89 residues was predicted. Based on this program, the predicted mature protein contains 361 amino acids with a predicted molecular mass of 40.6 kDa and an isoelectric pH of 8.87.

Example 2

Transformation of pSaMF37 into *Aspergillus oryzae* NRRL 3488

Protoplast preparation and transformation of *Aspergillus oryzae* NRRL3488 were performed by inoculating approximately $2\times10^7$ spores into 100 mL YEG medium and incubating the flask at 27° C. for 16-18 hours at 140 rpm. Mycelia were collected by pouring the culture through a sterile funnel lined with MIRACLOTH® (Calbiochem, San Diego, Calif., USA) and rinsing with 50 mL of 0.7 M KCl. The washed mycelia were resuspended in a 125 mL flask containing 20 mL of protoplasting solution composed of 5 mg GLUCANEX™ (Novozymes NS, Bagsvrd, Denmark) and 0.5 mg chitinase (Sigma Chemical Co., St. Louis, Mo., USA) per mL of 0.7 M KCl (filter sterilized) and incubated at 34° C. for 30 minutes with mixing at 80 rpm. The protoplasting solution was poured through a sterile funnel lined with MIRACLOTH® and rinsed with 50 mL of STC buffer (1 M sorbitol-10 mM Tris-HCl pH 6.5-10 mM $CaCl_2$). The flow-through was collected in two 50 mL polypropylene tubes. The tubes were centrifuged at 1300×g for 10 minutes at room temperature. The supernatant was discarded and the protoplast pellet was resuspended in 20 mL of STC buffer. The protoplasts were washed by two rounds of resuspending the pellet in 20 mL of STC buffer and centrifugation at 1300×g for 10 minutes at room temperature. The final pellet was resuspended in 2 mL of STC buffer. The protoplasts were counted by removing a 10 µl sample and counting them in a hemacytometer (VWR, West Chester, Pa., USA). The volume was adjusted with STC buffer to obtain a protoplast concentration of $2\times10^7$ per mL.

Plasmid pSaMF37 was prepared for transformation by restriction digestion with PmeI. The 5136 by expression cassette was separated from the digested vector by 0.8% agarose gel electrophoresis in TBE buffer and purified using a QIAQUICK® Gel Extraction Kit. Two transformation reactions were prepared. For each reaction, a 100 µL solution of protoplast preparation was transferred to a 12 mL polypropylene tube, to which was added 5 µg linearized pSaMF37, 250 µl PEG solution (60% w/v polyethylene glycol (PEG), 10 mM Tris 6.5, 10 mM CaCl) followed by gentle mixing and incubation at 37° C. for 30 minutes. Each transformation was diluted with 9 mL of STC buffer, followed by plating three separate 3 mL aliquots onto COVE plates. Each plate was then incubated at 34° C. for 7-10 days. Twenty SaMF37 transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 3

Production of Malic Acid in Shake Flask Cultures

Spores from transformants described above and *Aspergillus oryzae* NRRL 3488 as a control were plated onto individual COVE plates and allowed to sporulate at 34° C. for 5 to 7 days. Spores were collected in 0.1% TWEEN® 80 and counted using a hemacytometer. Seed cultures were prepared in 250 mL flasks containing 100 mL of seed medium B and inoculated with $2\times10^8$ total spores. Seed cultures were grown for approximately 17 hours at 30° C. with shaking at 200 rpm. Acid production cultures were prepared in 250 mL unbaffled flasks containing 50 mL of acid production medium C and 3 mL of the 17 hour seed cultures. Cultures were incubated at 30° C. with shaking at 200 rpm for 2-10 days.

Example 4

HPLC Quantitation of Malic Acid of Shake Flask Cultures

Quantitation of malic acid for the shake flask cultures of Example 3 was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125A 205×4.6 mm ID column and AQ C18 4×3.0 mm Security Guard Cartridge (Phenomenex, Inc., Torrance, Calif., USA). The HPLC Running Buffer consists of 10% methanol (HPLC grade) and 90% phosphate buffer (145 mM, pH 1.5).

Whole culture samples were removed and diluted 1:20 in HPLC Running Buffer composed. Approximately 270 µL of each sample was filtered through a 0.45 micron styrene 96 well filter plate (Millipore) prior to HPLC analysis.

RP-HPLC was performed using an injection volume of 10 µL at a flow rate of 0.7 mL/minute (isocratic) with a column temperature of 20° C. and run time of 14 minutes. Detection was set at 210 nm, 4 nm bandwidth, with the reference at 360 nm, 40 nm bandwidth. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was ≤5%. Malic acid shows $R^2 \geq 0.9999$ Approximately half of the 18 tested transformants above showed an increase in malic acid titer compared to malic acid production of *Aspergillus oryzae* NRRL 3488 as a control after 3 days of shake flask growth. Six transformants showed an increase of at least 40% relative to *Aspergillus oryzae* NRRL 3488.

Example 5

Fermentation of Transformed *Aspergillus oryzae* Strains

*Aspergillus oryzae* transformants above and the *Aspergillus oryzae* NRRL 3488 control are grown for approximately 7 days at 32° C. on PDA plates. A 5-6 mL volume of sterile 50 mM sodium phosphate buffer (pH 6.8) containing 0.1% TWEEN® 80 is added to each plate and spores are suspended by scraping with an inoculating loop. Each suspension is transferred by pipette to a 50 mL conical tube. For each tube, 25 mL of sterile sodium phosphate buffer is added to a 500 mL unbaffled flask containing 75 mL of seed medium, which is then inoculated with 2 mL of spore suspension. The seed medium is composed of 40g glucose, 4.0 g $(NH_4)_2SO_4$, 0.75 g $KH_2PO_4$, 0.75 g $K_2HPO_4$, 0.1 g $MgSO_4.7H_2O$, 0.1 g $CaCl_2.2H_2O$, 0.005 g $FeSO_4.7H_2O$, 0.005 g NaCl, and deionized water to 1 liter. The flasks are then incubated at 32° C. and 180 rpm for about 24 hours. The seed flasks are combined to supply the 144 mL inoculum required per tank.

Three-liter fermentors containing 1.8 liters of medium are individually inoculated by introducing 144 mL (8%) of the seed culture broth from the combined seed flasks of either an *Aspergillus oryzae* transformant or *Aspergillus oryzae* NRRL 3488. The medium is composed of 120g glucose, 90g $CaCO_3$, 6g Bacto peptone, 0.150g $KH_2PO_4$, 0.150 g $K_2HPO_4$, 0.10 g $MgSO.7H_2O$, 0.10 g $CaCl_2-2H_2O$, 0.005 g $FeSO_4.7H_2O$, 0.005 g NaCl, and deionized water to 1 liter.

The fermentors are equilibrated at 32±0.1° C. and stirred at 500 rpm. Inlet air flow is maintained at 1 v/v/m. No acid or base additions are used for pH control.

Samples are withdrawn daily and analyzed for malic acid production. Fermentations are completed after 7 days.

Example 6

HPLC Quantitation of Malic Acid of Fermentations

Quantitation of malic acid for the fermentations of Example 5 is performed as described in Example 4. The relative changes in malic acid titer during fermentation is demonstrated for the transformants above compared to malic acid production of *Aspergillus oryzae* NRRL 3488.

The present invention may be further described by the following numbered paragraphs:

[1] A method of producing a C4 dicarboxylic acid, comprising:
(a) cultivating a host cell comprising a heterologous polynucleotide encoding a C4 dicarboxylic acid transporter; wherein the transporter is selected from:
(i) a C4 dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
(ii) a C4 dicarboxylic acid transporter encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof;
(iii) a C4 dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 3;
(iv) a C4 dicarboxylic acid transporter variant comprising a substitution, deletion, and/or insertion of one or more (e.g., two, several) amino acids of the mature polypeptide of SEQ ID NO: 2; and
(v) a fragment of the C4 dicarboxylic acid transporter of (i), (ii), (iii), or (iv) that has C4 dicarboxylic acid transporter activity; and
(b) recovering the C4 dicarboxylic acid.

[2] The method of paragraph [1], wherein the C4 dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

[3] The method of paragraph [1] or [2], wherein the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1 or SEQ ID NO: 3, or the full-length complementary strand thereof.

[4] The method of any one of paragraphs [1]-[3], wherein the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3.

[5] The method of any one of paragraphs [1]-[4], wherein the C4 dicarboxylic acid transporter comprises or consists of SEQ ID NO: 2.

[6] The method of any one of paragraphs [1]-[4], wherein the C4 dicarboxylic acid transporter comprises or consists of the mature polypeptide of SEQ ID NO: 2.

[7] The method of paragraph [6], wherein the mature polypeptide of SEQ ID NO: 2 is amino acids 58 to 450 of SEQ ID NO: 2 or amino acids 90 to 450 of SEQ ID NO: 2.

[8] The method of any one of paragraphs [1]-[4], wherein the C4 dicarboxylic acid transporter is a fragment of SEQ ID NO: 2, wherein the fragment has C4 dicarboxylic acid transporter activity.

[9] The method of any one of paragraphs [1]-[4], wherein the C4 dicarboxylic acid transporter is a variant comprising a substitution, deletion, and/or insertion of one or more (e.g., two, several) amino acids of the mature polypeptide of SEQ ID NO: 2.

[10] The method of any one of paragraphs [1]-[9], wherein the heterologous polynucleotide encoding the C4 dicarboxylic acid transporter is operably linked to a promoter foreign to the polynucleotide.

[11] The method of any one of paragraphs [1]-[10], wherein the host cell further comprises a heterologous second polynucleotide encoding a malate dehydrogenase.

[12] The method of paragraph [11], wherein the heterologous second polynucleotide encoding a malate dehydrogenase is operably linked to a promoter foreign to the polynucleotide.
[13] The method of any one of paragraphs [1]-[12], wherein the host cell further comprises a heterologous third polynucleotide encoding a pyruvate carboxylase.
[14] The method of paragraph [13], wherein the heterologous third polynucleotide encoding a pyruvate carboxylase is operably linked to a promoter foreign to the polynucleotide.
[15] The method of any one of paragraphs [1]-[14], wherein the host cell is a filamentous fungal host cell.
[16] The method of paragraph [15], wherein the host cell is selected from an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, and *Trichoderma* cell.
[17] The method of paragraph [16], wherein the host cell is an *Aspergillus* host cell.
[18] The method of paragraph [17], wherein the *Aspergillus* host cell is an *Aspergillus oryzae* host cell.
[19] The method of any one of paragraphs [1]-[18], wherein the level of the C4 dicarboxylic acid is increased by at least 25%, e.g., at least 50%, at least 100%, at least 150%, at least 200%, at least 300%, or at 500% compared to the host cell without the heterologous polynucleotide encoding the C4 dicarboxylic acid transporter when cultivated under the same conditions.
[20] The method of any one of paragraphs [1]-[19], wherein the C4 dicarboxylic acid is selected from malic acid, succinic acid, oxaloacetic acid, malonic acid, and fumaric acid.
[21] The method of paragraph [20], wherein the C4 dicarboxylic acid is malic acid.
[22] A method for increasing C4 dicarboxylic acid production, comprising:
   (a) transforming into a host cell a heterologous polynucleotide encoding a C4 dicarboxylic acid transporter; wherein the transporter is selected from:
      (i) a C4 dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
      (ii) a C4 dicarboxylic acid transporter encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof;
      (iii) a C4 dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 3;
      (iv) a C4 dicarboxylic acid transporter variant comprising a substitution, deletion, and/or insertion of one or more (e.g., two, several) amino acids of the mature polypeptide of SEQ ID NO: 2; and
      (v) a fragment of the C4 dicarboxylic acid transporter of (i), (ii), (iii), or (iv) that has C4 dicarboxylic acid transporter activity; and
   (b) cultivating the transformed organism in a medium; and
   (c) recovering the C4 dicarboxylic acid.
[23] The method of paragraph [22], wherein the C4 dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.
[24] The method of paragraph [22] or [23], wherein the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof.
[25] The method of any one of paragraphs [22]-[24], wherein the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3.
[26] The method of any one of paragraphs [22]-[25], wherein the C4 dicarboxylic acid transporter comprises or consists of SEQ ID NO: 2.
[27] The method of any one of paragraphs [22]-[25], wherein the C4 dicarboxylic acid transporter comprises or consists of the mature polypeptide of SEQ ID NO: 2.
[28] The method of paragraph [27], wherein the mature polypeptide of SEQ ID NO: 2 is amino acids 58 to 450 of SEQ ID NO: 2 or amino acids 90 to 450 of SEQ ID NO: 2.
[29] The method of any one of paragraphs [22]-[25], wherein the C4 dicarboxylic acid transporter is a fragment of SEQ ID NO: 2, wherein the fragment has C4 dicarboxylic acid transporter activity.
[30] The method of any one of paragraphs [22]-[25], wherein the C4 dicarboxylic acid transporter is a variant comprising a substitution, deletion, and/or insertion of one or more (e.g., two, several) amino acids of the mature polypeptide of SEQ ID NO: 2.
[31] The method of any one of paragraphs [22]-[30], wherein the heterologous polynucleotide encoding the C4 dicarboxylic acid transporter is operably linked to a promoter foreign to the polynucleotide.
[32] The method of any one of paragraphs [22]-[31], wherein the host cell further comprises a heterologous second polynucleotide encoding a malate dehydrogenase.
[33] The method of paragraph [32], wherein the heterologous second polynucleotide encoding a malate dehydrogenase is operably linked to a promoter foreign to the polynucleotide.
[34] The method of any one of paragraphs [22]-[33], wherein the host cell further comprises a heterologous third polynucleotide encoding a pyruvate carboxylase.
[35] The method of paragraph [34], wherein the heterologous third polynucleotide encoding a pyruvate carboxylase is operably linked to a promoter foreign to the polynucleotide.
[36] The method of any one of paragraphs [22]-[35], wherein the host cell is a filamentous fungal host cell.
[37] The method of paragraph [36], wherein the host cell is selected from an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, and *Trichoderma* cell.
[38] The method of paragraph [37], wherein the host cell is an *Aspergillus* host cell.

[39] The method of paragraph [38], wherein the *Aspergillus* host cell is an *Aspergillus oryzae* host cell.

[40] The method of any one of paragraphs [22]-[39], wherein the level of the C4 dicarboxylic acid is increased by at least 25%, e.g., at least 50%, at least 100%, at least 150%, at least 200%, at least 300%, or at 500% compared to the host cell without the heterologous polynucleotide encoding the C4 dicarboxylic acid transporter when cultivated under the same conditions.

[41] The method of any one of paragraphs [22]-[40], wherein the C4 dicarboxylic acid is selected from malic acid, succinic acid, oxaloacetic acid, malonic acid, and fumaric acid.

[42] The method of paragraph [41], wherein the C4 dicarboxylic acid is malic acid.

[43] A host cell comprising a heterologous polynucleotide encoding a C4 dicarboxylic acid transporter, wherein the transporter is selected from:

(a) a C4 dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a C4 dicarboxylic acid transporter encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof;

(c) a C4 dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 3;

(d) a C4 dicarboxylic acid transporter variant comprising a substitution, deletion, and/or insertion of one or more (e.g., two, several) amino acids of the mature polypeptide of SEQ ID NO: 2; and (e) a fragment of the C4 dicarboxylic acid transporter of (a), (b), (c), or (d) that has C4 dicarboxylic acid transporter activity;

wherein the host cell secretes increased levels of C4 dicarboxylic acid compared to the host cell without the heterologous polynucleotide encoding the C4 dicarboxylic acid transporter when cultivated under the same conditions.

[44] The host cell of paragraph [43], wherein the C4 dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

[45] The host cell of paragraph [43] or [44], wherein the C4 dicarboxylic acid transporter is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1, SEQ ID NO: 3, or the full-length complementary strand thereof.

[46] The host cell of any one of paragraphs [43]-[45], wherein the C4 dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3.

[47] The host cell of any one of paragraphs [43]-[46], wherein the C4 dicarboxylic acid transporter comprises or consists of SEQ ID NO: 2.

[48] The host cell of any one of paragraphs [43]-[46], wherein the C4 dicarboxylic acid transporter comprises or consists of the mature polypeptide of SEQ ID NO: 2.

[49] The host cell of paragraph [48], wherein the mature polypeptide of SEQ ID NO: 2 is amino acids 58 to 450 of SEQ ID NO: 2 or amino acids 90 to 450 of SEQ ID NO: 2.

[50] The host cell of any one of paragraphs [43]-[46], wherein the C4 dicarboxylic acid transporter is a fragment of SEQ ID NO: 2, wherein the fragment has C4 dicarboxylic acid transporter activity.

[51] The host cell of any one of paragraphs [43]-[46], wherein the C4 dicarboxylic acid transporter is a variant comprising a substitution, deletion, and/or insertion of one or more (e.g., two, several) amino acids of the mature polypeptide of SEQ ID NO: 2.

[52] The host cell of any one of paragraphs [43]-[51], wherein the heterologous polynucleotide encoding the C4 dicarboxylic acid transporter is operably linked to a promoter foreign to the polynucleotide.

[53] The host cell of any one of paragraphs [43]-[52], wherein the host cell further comprises a heterologous second polynucleotide encoding a malate dehydrogenase.

[54] The host cell of paragraph [53], wherein the heterologous second polynucleotide encoding a malate dehydrogenase is operably linked to a promoter foreign to the polynucleotide.

[55] The host cell of any one of paragraphs [43]-[54], wherein the host cell further comprises a heterologous third polynucleotide encoding a pyruvate carboxylase.

[56] The host cell of paragraph [55], wherein the heterologous third polynucleotide encoding a pyruvate carboxylase is operably linked to a promoter foreign to the polynucleotide.

[57] The host cell of any one of paragraphs [43]-[56], wherein the host cell is a filamentous fungal host cell.

[58] The host cell of paragraph [57], wherein the host cell is selected from an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma* cell.

[59] The host cell of paragraph [58], wherein the host cell is an *Aspergillus* host cell.

[60] The host cell of any one of paragraphs [59], wherein the *Aspergillus* host cell is an *Aspergillus oryzae* host cell.

[61] The host cell of any one of paragraphs [43]-[60], wherein the host cell is capable of secreting an increased level of the C4 dicarboxylic acid of at least 25%, e.g., at least 50%, at least 100%, at least 150%, at least 200%, at least 300%, or at 500% compared to the host cell without the polynucleotide encoding the heterologous polynucleotide when cultivated under the same conditions.

[62] The host cell of any one of paragraphs [43]-[61], wherein the C4 dicarboxylic acid is selected from malic acid, succinic acid, oxaloacetic acid, malonic acid, and fumaric acid.

[63] The host cell of paragraph [62], wherein the C4 dicarboxylic acid is malic acid.

What is claimed is:

1. A filamentous fungal host cell comprising a heterologous polynucleotide encoding a C4 dicarboxylic acid transporter, wherein the heterologous polynucleotide:
   (a) encodes a C4 dicarboxylic acid transporter having at least 95% sequence identity to the mature polypeptide of SEQ ID NO: 2;
   (b) hybridizes under high stringency conditions with the full-length complementary strand of SEQ ID NO: 1 or SEQ ID NO: 3; or
   (c) has at least 95% sequence identity to the mature polypeptide coding sequence of SEQ ID NO: 1 or SEQ ID NO: 3;

wherein the host cell secretes increased levels of C4 dicarboxylic acid compared to the host cell without the heterologous polynucleotide encoding the C4 dicarboxylic acid transporter when cultivated under the same conditions.

2. The filamentous fungal host cell of claim 1, wherein the heterologous polynucleotide encodes a C4 dicarboxylic acid transporter having at least 95% sequence identity to the mature polypeptide of SEQ ID NO: 2.

3. The filamentous fungal host cell of claim 1, wherein the heterologous polynucleotide encoding the C4 dicarboxylic acid transporter hybridizes under very high stringency conditions with the full-length complementary strand of SEQ ID NO: 1 or SEQ ID NO: 3.

4. The filamentous fungal host cell of claim 1, wherein the heterologous polynucleotide encodes a C4 dicarboxylic acid transporter that comprises or consists of the mature polypeptide of SEQ ID NO: 2.

5. The filamentous fungal host cell of claim 1, wherein the mature polypeptide of SEQ ID NO: 2 is amino acids 58 to 450 or amino acids 90 to 450 of SEQ ID NO: 2.

6. The filamentous fungal host cell of claim 1, wherein the heterologous polynucleotide encodes a C4 dicarboxylic acid transporter that comprises or consists of SEQ ID NO: 2.

7. The filamentous fungal host cell of claim 1, wherein the heterologous polynucleotide encoding the C4 dicarboxylic acid transporter is operably linked to a promoter foreign to the polynucleotide.

8. The filamentous fungal host cell of claim 1, wherein the host cell further comprises a heterologous polynucleotide encoding a malate dehydrogenase.

9. The filamentous fungal host cell of claim 1, wherein the host cell further comprises a heterologous polynucleotide encoding a pyruvate carboxylase.

10. The filamentous fungal host cell of claim 1, wherein the host cell is selected from an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, and *Trichoderma* cell.

11. The filamentous fungal host cell of claim 10, wherein the host cell is an *Aspergillus* host cell.

12. The filamentous fungal host cell of claim 11, wherein the *Aspergillus* host cell is an *Aspergillus oryzae* host cell.

13. The filamentous fungal host cell of claim 1, wherein the host cell secretes at least 25% more C4 dicarboxylic acid compared to the host cell without the polynucleotide encoding the C4 dicarboxylic acid transporter when cultivated under the same conditions.

14. The filamentous fungal host cell of claim 1, wherein the C4 dicarboxylic acid is malic acid.

15. A method of producing a C4 dicarboxylic acid, comprising:
(a) cultivating the filamentous fungal host cell of claim 1 in a medium; and
(b) recovering the C4 dicarboxylic acid.

16. The method of claim 15, wherein the C4 dicarboxylic acid is malic acid.

17. The filamentous fungal host cell of claim 1, wherein the host cell secretes at least 40% more C4 dicarboxylic acid compared to the host cell without the polynucleotide encoding the C4 dicarboxylic acid transporter when cultivated under the same conditions.

18. The filamentous fungal host cell of claim 1, wherein the heterologous polynucleotide encoding the C4 dicarboxylic acid transporter comprises or consists of the mature polypeptide coding sequence of SEQ ID NO: 1 or SEQ ID NO: 3.

19. The filamentous fungal host cell of claim 1, wherein the heterologous polynucleotide encodes a C4 dicarboxylic acid transporter having at least 97% sequence identity to the mature polypeptide of SEQ ID NO: 2.

20. The filamentous fungal host cell of claim 1, wherein the heterologous polynucleotide encodes a C4 dicarboxylic acid transporter having at least 98% sequence identity to the mature polypeptide of SEQ ID NO: 2.

21. The filamentous fungal host cell of claim 1, wherein the heterologous polynucleotide encodes a C4 dicarboxylic acid transporter having at least 99% sequence identity to the mature polypeptide of SEQ ID NO: 2.

22. The filamentous fungal host cell of claim 1, wherein the heterologous polynucleotide encodes a C4 dicarboxylic acid transporter that comprises or consists of amino acids 58 to 450 or amino acids 90 to 450 of SEQ ID NO: 2.

23. The filamentous fungal host cell of claim 1, wherein the heterologous polynucleotide encoding the C4 dicarboxylic acid transporter hybridizes under high stringency conditions with the full-length complementary strand of SEQ ID NO: 1 or SEQ ID NO: 3.

24. The filamentous fungal host cell of claim 1, wherein the heterologous polynucleotide has at least 95% sequence identity to the mature polypeptide coding sequence of SEQ ID NO: 1 or SEQ ID NO: 3.

25. The filamentous fungal host cell of claim 1, wherein the heterologous polynucleotide has at least 97% sequence identity to the mature polypeptide coding sequence of SEQ ID NO: 1 or SEQ ID NO: 3.

26. The filamentous fungal host cell of claim 1, wherein the heterologous polynucleotide has at least 98% sequence identity to the mature polypeptide coding sequence of SEQ ID NO: 1 or SEQ ID NO: 3.

27. The filamentous fungal host cell of claim 1, wherein the heterologous polynucleotide has at least 99% sequence identity to the mature polypeptide coding sequence of SEQ ID NO: 1 or SEQ ID NO: 3.

28. A filamentous fungal host cell comprising a heterologous polynucleotide encoding a C4 dicarboxylic acid transporter, wherein:
the heterologous polynucleotide is operably linked to a promoter foreign to the polynucleotide;
the heterologous polynucleotide encodes a C4 dicarboxylic acid transporter having at least 95% sequence identity to amino acids 58 to 450 or amino acids 90 to 450 of SEQ ID NO: 2; and
the host cell is capable of secreting increased levels of C4 dicarboxylic acid compared to the host cell without the heterologous polynucleotide encoding the C4 dicarboxylic acid transporter when cultivated under the same conditions.

\* \* \* \* \*